United States Patent [19]

Veatch

[11] Patent Number: 5,214,035
[45] Date of Patent: May 25, 1993

[54] THIXOTROPIC FORMULATIONS
[75] Inventor: James L. Veatch, Asbury, N.J.
[73] Assignee: Hoechst-Roussel Agri-Vet Company, Somerville, N.J.
[21] Appl. No.: 869,586
[22] Filed: Apr. 16, 1992
[51] Int. Cl.$^5$ ............................................. A61K 31/575
[52] U.S. Cl. .................................................... 514/179
[58] Field of Search .......................................... 514/179

[56] References Cited

U.S. PATENT DOCUMENTS

| | | | |
|---|---|---|---|
| 3,860,701 | 1/1975 | Short et al. | 514/179 |
| 4,196,218 | 4/1980 | Thiele . | |
| 4,576,645 | 3/1986 | Ravel et al. . | |
| 4,609,651 | 9/1986 | Rohde et al. | 514/179 |
| 4,661,524 | 4/1987 | Thomson et al. . | |
| 4,891,365 | 1/1990 | Wiechert et al. | 514/179 |

OTHER PUBLICATIONS

Merck Index, 10th edition, 309 (1983).

Primary Examiner—Marianne M. Cintins
Assistant Examiner—John Peabody
Attorney, Agent, or Firm—Barbara V. Maurer

[57] ABSTRACT

This application relates to a novel thixotropic formulation of a compound which suppresses estrus in animals, which formulation allows for convenient, accurate dosing of the animal when treated with the compound.

11 Claims, No Drawings

THIXOTROPIC FORMULATIONS

This application relates to a novel formulation of a compound which suppresses estrus in animals, which formulation allows for convenient, accurate dosing of the animal when treated with the compound.

Altrenogest (17hydroxy-17-(2-propenyl)estra-4,9,11-trien-3-one) is known to be effective in suppressing estrus in animals, particularly horses and swine. However, the compound also can cause a physiological reaction in humans. Therefore it is imperative that a person dosing an animal not come into contact with the formulated compound.

The known formulations of altrenogest are difficult to use. They typically are oily compositions, such as suspensions in neobee oil, which can hold a static charge. Thus administration of the known formulations is often fraught with spills, drips on the person administering the dose and lost material. There remains a need for a formulation of altrenogest which is stable, easy to use and is not susceptible undesired drips.

It is accordingly the object of this invention to provide a unique, novel and easy to use composition which is useful in dosing animals without the mess of spills or the loss of great amounts of material. This and other objects of the invention will become apparent to those skilled in the art from the following detailed description.

This invention relates to a unique, novel and easy to use composition which is useful in dosing animals without spills thus delivering more exact dosages. More particularly, the invention provides a thixotropic gel which can be administered orally, preferably by syringe, which gel is a non-aerated composition comprising active estrus suppressing ingredient in an amount effective to suppress estrus, solvent and gelling agent and has an RVT Brookfield static viscosity of from about 100,000 to about 700,000 cps at room temperature.

Gels are used for a variety of products, including veterinary products. Thixotropic gels have the property of being semisolid colloids (gels) when undisturbed, but flowing readily when shaken, stirred, sheared or otherwise subjected to stress. Such gels typically are prepared by mixing a solvent, optionally a cosolvent, gelling agent and active ingredient as well as other additives under conditions in which the mixture is either a liquid solution or a suspension. The mixture is then cooled causing a gel to form, accompanied in some cases by polymerization or other reaction between various substituents. The final gel is a semisolid suspension. Only some gels formed in this manner are stable and exhibit good thixotropy; many either separate with time (being too thin) or do not yield to shear (being too thick). Additionally many mixtures of components fail to form or retain a colloidal state and droplets of one or more components separate upon cooling. Depending on the concentration, the physical properties of the active ingredient may also impact on the stability of the gel.

The term "compatible" as used in this application relates to the stability of the gel at a controlled room temperature of from about 40° F. (4.4° C.) to about 90° F. (32° C.), preferably from about 55° F. (15° C.) to about 86° F. (30° C.), where the gel does not separate into visibly distinct phases or become visably grainy. Thus an incompatible mixture wills show droplets or grains when pressed between two microscope slides or exhibit excessive cloudiness compared to compatible gels.

The term "stable" as used in this application relates to the flow characteristics of the gel, i.e. the gel does not readily flow in the absence of shear and further remains compatible over a broad temperature range of from about 40° F. (4.4° C.) to about 90° F. (32° C.). Freezing destroys the composition.

The term "thixotropic" as used in this application relates to the common meaning of spreading or flowing with stress, but remaining stable in the absence of stress.

The stable thixotropic gel of the instant invention can be prepared by heating a portion of the solvent, for example, a glyceride solvent such as caprylic/capric triglyceride ("Neobee M-5"), dissolving the active ingredient in the heated solvent with stirring and forming a solution. The solution is then added to additional warmed solvent and gelling agent such as, for example, colloidal silicon dioxide, is added with stirring.

In a preferred embodiment of the invention, additives such as oxidants, for example, butylated hydroxyanisole (BHA) and butylated hydroxytoluene (BHT), and preservatives, for example, sorbic acid and benzyl alcohol are added to the composition. Preferably, BHA, BHT and sorbic acid are added to the warm solvent before the active ingredient and benzyl alcohol is added to the solution of active ingredient before the gelling agent is added.

In general, the solvent is about 85-95 weight percent of the composition, preferably about 89-93 weight percent, most preferably about 90-91 weight percent. The active ingredient is generally about 0.05-0.5 weight percent of the composition, preferably about 0.1-0.3 weight percent, most preferably about 0.2-0.25 weight percent. The gelling agent is generally about 4-12 weight percent of the composition, preferably about 6-10 weight percent, most preferably about 8 weight percent.

For a 0.215% active ingredient gel the quantitative composition and ranges for the inactive components are:

| Component | Amount mg/g | Ranges, mg/g |
| --- | --- | --- |
| Altrenogest | 2.149 | — |
| BHT | 0.068 | 0.065–0.071 |
| BHA | 0.068 | 0.065–0.071 |
| Sorbic Acid | 1.465 | 1.392–1.583 |
| Benzyl Alcohol | 9.767 | 9.279–10.255 |
| Colloidal Silicon Dioxide | 80.000 | 76.000–84.000 |
| Caprylic/Capric Triglyceride | 906.483 | 861.159–951.807 |
| Total Weight | 1000.000 | |

The composition of the invention can then be placed in a dispensing apparatus. In a preferred embodiment of this invention, the composition is placed in a multidose plastic syringe which is then used when dosing an animal. In this embodiment, the physical properties of the composition are such that the composition flows readily from the syringe when pressure is placed on the plunger, but does not leak or flow from the syringe when the pressure is removed from the plunger.

In order to further illustrate the present invention, various examples are set forth below. In these examples, as throughout this specification and claims all temperatures are in degrees centigrade and all parts and percentages are by weight unless otherwise specified.

EXAMPLE 1

"Neobee M-5" (58,921.4 g) was heated to 50°-55° C. and butylated hydroxy anisole (BHA) (4.42 g, butylated hydroxytoluene (BHT) (4.42 g), and sorbic acid (95.2 g) were added with stirring to effect a solution. Then there was added altrenogest (139.7 g) and the mixture was stirred until a solution is formed. While still mixing slowly, benzyl alcohol (634.8 g) was added and the mixture was stirred until a solution was formed. To this mixture there was added slowly while mixing colloidal silicon dioxide (5,200 g) and the mixture was stirred thoroughly to effect a homogeneous gel.

EXAMPLE 2

In a main processing vessel there is added "Neobee M-5" (241,944.0 g) and the contents are heated until the temperature reaches 56° C. In another container "Neobee M-5" (30,000 g) is heated to 78° C. and BHA (20.4 g), BHT (20.4 g) and sorbic acid (439.5 g) is added slowly with mixing to effect a solution. With mixing stopped there is added altrenogest (644.7 g) carefully to avoid "dusting" to the air, then the mixing is continued until a solution is effected. This solution is then added to the heated "Neobee M-5" in the main processing vessel. Then there is added benzyl alcohol (2,930.1 g) with stirring to effect a homogeneous solution. Then there is added colloidal silicon dioxide (24,000 g) and the mixture is stirred to disperse the material completely and without lumps while avoiding aeration of the final product.

EXAMPLE 3

A 60 g multidose plastic syringe is filled with the composition of Example 2, an amount sufficient to treat one 1100 pound (500 kg) horse daily for 5 days. Each division on the syringe constitutes one daily dose (10.24 g) of altrenogest (0.215 g). The dose is administered by removing the syringe tip, turning the dial ring on the syringe until the edge of the ring lines up with zero, depressing the plunger to advance the gel to the tip, advancing the dial ring to the first division mark on the plunger, inserting the nozzle of the syringe through the interdental space in a mare's mouth (which is free of food) and depositing the gel on the back of the tongue by depressing the plunger until it stops, removing the syringe and replacing the tip.

A second through fifth dose is administered from the same syringe by advancing the dial ring to the next division mark and repeating the procedure outlined above.

It should be understood that this specification and examples are set forth by way of illustration and not limitation and that various modifications and changes may be made without departing from the spirit and scope of the present invention as defined by the appended claims.

I claim:

1. A stable, gel which can be administered to animals orally by syringe, which gel is a non-aerated composition comprising an effective amount of estrus suppressing active ingredient, solvent and gelling agent and has an RVT Brookfield static viscosity of from about 100,000 to about 700,000 cps at room temperature wherein said active ingredient is altrenogest.

2. The gel of claim 1 which comprises 85-95 weight percent of solvent, 0.05-0.5 weight percent of active ingredient and 4-12 weight percent of gelling agent.

3. The gel of claim 2 which comprises 89-93 weight percent of solvent, 0.1-0.3 weight percent of active ingredient and 6-10 weight percent of gelling agent.

4. The gel of claim 3 which comprises 90-91 weight percent of solvent, 0.2-0.25 weight percent of active ingredient and about 8 weight percent of gelling agent.

5. The gel of claim 1 wherein the solvent is caprylic-/capric triglyceride and the gelling agent is colloidal silicon dioxide.

6. The gel of claim 5 which further comprises oxidants and preservatives.

7. The gel of claim 6 wherein the oxidants are butylated hydroxyanisole and butylated hydroxytoluene and the preservatives are sorbic acid and benzyl alcohol.

8. The gel of claim 7 which comprises 85-95 weight percent of solvent, 0.05-0.5 weight percent of active ingredient and 4-12 weight percent of gelling agent.

9. The gel of claim 8 which comprises 89-93 weight percent of solvent, 0.1-0.3 weight percent of active ingredient and 6-10 weight percent of gelling agent.

10. The gel of claim 9 which comprises 90-91 weight percent of solvent, 0.2-0.25 weight percent of active ingredient and about 8 weight percent of gelling agent.

11. The gel of claim 10 having about 0.215% active ingredient and ranges for the inactive components of:

| Component | Relative Amount, mg or g | Ranges, mg or g |
|---|---|---|
| Altrenogest | 2.149 | — |
| BHT | 0.068 | 0.065–0.071 |
| BHA | 0.068 | 0.065–0.071 |
| Sorbic Acid | 1.465 | 1.392–1.583 |
| Benzyl Alcohol | 9.767 | 9.279–10.255 |
| Colloidal Silicon Dioxide | 80.000 | 76.000–84.000 |
| Caprylic/Capric Triglyceride | 906.483 | 861.159–951.807 |
| Total Weight | 1000.000 | |

* * * * *